(12) United States Patent
Metelski

(10) Patent No.: US 6,679,470 B2
(45) Date of Patent: Jan. 20, 2004

(54) MICROSCOPE STAND, IN PARTICULAR FOR A SURGICAL MICROSCOPE

(75) Inventor: Andrzej Metelski, Romanshorn (CH)

(73) Assignee: Leica Microsystems (Schweiz) AG, Heerbrugg (CH)

(*) Notice: Subject to any disclaimer, the term of this patent is extended or adjusted under 35 U.S.C. 154(b) by 0 days.

(21) Appl. No.: 10/107,464

(22) Filed: Mar. 27, 2002

(65) Prior Publication Data

US 2002/0166942 A1 Nov. 14, 2002

(30) Foreign Application Priority Data

Mar. 31, 2001 (DE) .......................... 101 15 837

(51) Int. Cl.⁷ .............................................. F16M 19/00
(52) U.S. Cl. ...................................................... 248/676
(58) Field of Search .............................. 248/562, 278.1, 248/676, 636, 610; 74/573 R, 574, 572, 604; 901/48; 414/719; 359/384, 382, 368

(56) References Cited

U.S. PATENT DOCUMENTS

| | | | |
|---|---|---|---|
| 5,173,803 A | | 12/1992 | Heller |
| 5,366,193 A | * | 11/1994 | Lindsay ................... 248/183.2 |
| 5,528,417 A | | 6/1996 | Nakamura |
| 6,162,523 A | | 12/2000 | Metelski et al. |
| 6,364,268 B1 | * | 4/2002 | Metelski ..................... 248/317 |
| 6,392,795 B2 | * | 5/2002 | Okada ........................ 359/368 |

FOREIGN PATENT DOCUMENTS

| | | |
|---|---|---|
| DE | 42 14 858 C1 | 10/1994 |
| WO | WO 98/53244 | 11/1998 |

* cited by examiner

Primary Examiner—Leslie A. Braun
Assistant Examiner—Kofi Schulterbrandt
(74) Attorney, Agent, or Firm—Hodgson Russ LLP

(57) ABSTRACT

The invention concerns a novel stand in which at least one support (1, 2) is torsionally vibration-damped with respect to another (2, 1).

14 Claims, 6 Drawing Sheets

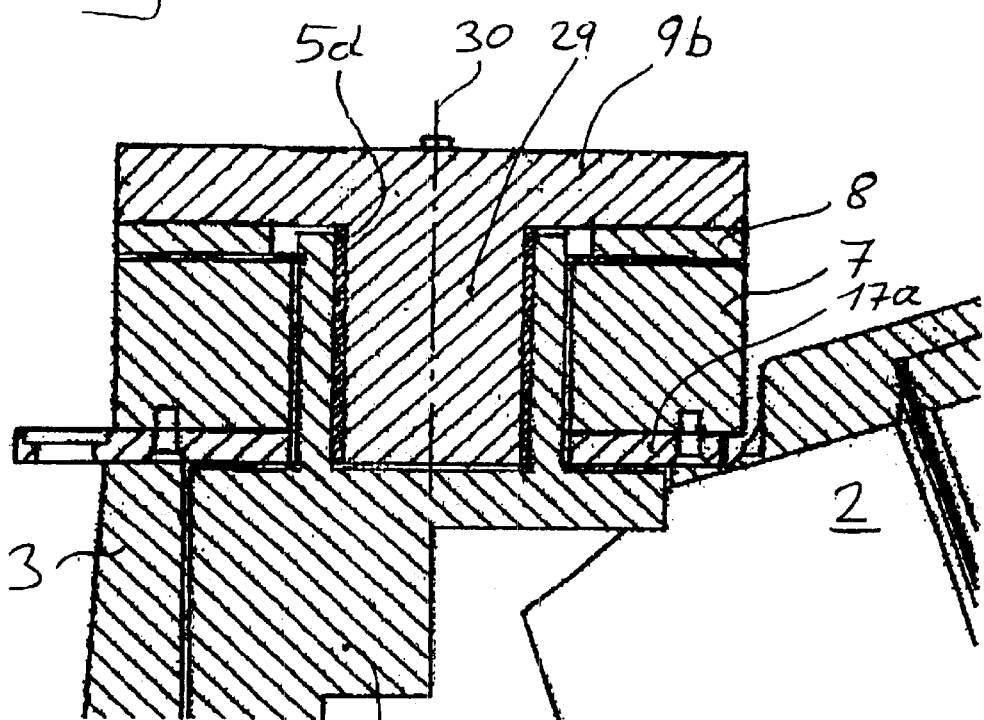
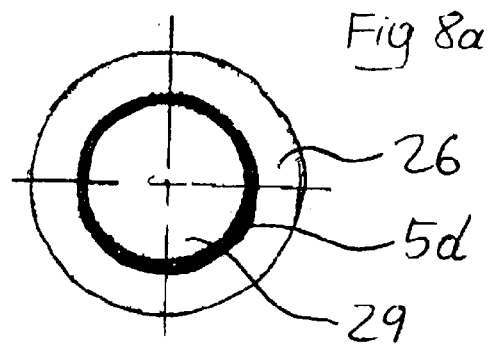

MICROSCOPE STAND, IN PARTICULAR FOR A SURGICAL MICROSCOPE

CROSS REFERENCE TO RELATED APPLICATIONS

This application claims priority of the German patent application 101 15 837.8 which is incorporated by reference herein.

FIELD OF THE INVENTION

The invention concerns a stand, in particular for a surgical microscope. The purpose of such stands is to hold a relatively heavy microscope so that it is movable by an operator with a minimum of resistance. An effort is therefore made to configure all joints, bearings, and the like in as low-resistance a fashion as possible, so that as little resistance as possible is presented to any arbitrary movement by the user.

BACKGROUND OF THE INVENTION

In surgery but also in other areas of technology, for example microelectronics, forensics, etc., more and more use is being made of surgical microscopes that, because of their heavy weight, must be supported by stands. Several well-known manufacturers have marketed stands that are well suited, in terms of mechanics and statics, for supporting the load of a surgical microscope. The present applicant, for example, markets stands with the designation OHS or MS1. One example of such a stand is found in EP-A-628290. Zeiss/Deutschland has disclosed a stand, for example, in EP-476552.

Many modern stands have parallelogram supports to allow the load of the surgical microscopes to be carried over the greatest possible distances with no bending or twisting, in order to maximize the freedom of movement and radius of action of the microscopes. In principle, however, the greater the radius of action, the greater the instability of a stand, except if appropriate design actions are taken against instability. However, the more rigid (less unstable) the structures, the more susceptible they are to vibratory behavior, which is similarly counteracted with design features such as selection of varying tube cross sections, material selection, use of damping elements, etc.

The transported weight of the stands also represents a problem whose solution lies fundamentally in weight reduction by means of high-strength materials.

For example, the present applicant has created a stand that uses at least one support made of a fiber-reinforced plastic. This stand is described in the aforementioned WO-A-97/20166.

It has been recognized, however, that weight reduction alone is not sufficient in some circumstances if the quality of the damping properties of the essential components is not sufficiently taken into account. Mere weight reduction results in some circumstances in intensified, higher-frequency vibratory behavior in the structure. This vibratory behavior is amplified in structures having braked arms. Brakes of this kind are to be operated electromagnetically, pneumatically, or even by hand, and create a rigid connection between the components, so that vibrations are transmitted from one component to another and result in a long vibration period that is annoying to the user.

The route of weight reduction by means of fiber composite materials and plastics has been taken in another sector of stand design, namely X-ray technology, as set forth in DE-C1-42 14 858. In this, a C-curve was created from plastic foam as the supporting part that determines the shape, which is surrounded by a fiber-reinforced plastic that assumes the support functions. If this known assemblage is to be particularly light in weight, then according to this previously published teaching a profile of closed shape must be produced from (only) fiber-reinforced plastic. Composite material structures of this kind have inherently low vibratory characteristics.

In stands for the applications mentioned, however, there exist joints, rotary bearings and the like in which vibratory behavior can occur regardless of the quality of the other components. One such point, for example, is the vertical rotary bearing on a vertical upright column for the horizontal carrier arm or arms of the stand. Proceeding from such bearing points, which as a rule can be immobilized using brakes, movements or forces on the microscope also create torsional forces which in turn can preferentially excite torsional vibrations in the components that are loaded in torsion.

For particular vibration damping, the present applicant has already offered solutions that are recited, for example, in WO-A-98/53244. In this, inter alia, elastically damping layers which act to damp the vibration chain from the microscope to the floor are installed under the mounting feet of the tripod foot. With these known assemblages, even the slightest change in the position of the microscope causes a vibratory excitation which nevertheless, once it has passed through the stand, is damped at the mounting feet and therefore reflected only in attenuated fashion.

Damping plates that are inserted between stand components have also been proposed, for example damping shoes at the transition from a support tube to a support tube mount, or damping plates between two flanges of two adjacent support tubes or between a tube and a pedestal.

The advantage of such damping elements in the region of the upper body of the stand is that they help damp the vibrations on their initial path from the microscope to the floor, so that need not even pass through the entire stand. The effectiveness of these known damping shims lies in the damping effect that occurs upon compression of these damping elements, i.e. for example when the tube vibrates in its shoe in the axial direction of the tube or in a direction perpendicular thereto (tilting vibration), or if the mounting feet are loaded in terms of pressure load fluctuations due to vibration of the upright column in a vertical plane.

Attempts to damp torsional vibrations have hitherto been made by way of a particular configuration of the support tubes. For example, aluminum/composite plastic tubes or carbon fiber-reinforced plastic tubes have been created, in which torsion in the tube was counteracted by specific selection of the fiber plies. The OHS of the present applicant that is configured in this fashion has low torsional behavior, however, not only as a result of good selection of the supports, but also because of the balanced configuration about the rotation axis in the upright column. In this known assemblage, the center of gravity of the moving carrier arms and balancing arms lies directly above or in the immediate vicinity of the upright column. Other stands in which the center of gravity of the moving carrier arms is well to the side of the upright column amplify the torsional vibration behavior, especially if the stand is braked via the rotation axis. Mere application or release of the brake, or the slightest movements of the microscope, can generate torsional vibrations.

Torsional vibrations (often horizontal vibrations) are substantially more deleterious in microscopy than vertical vibrations, in particular because in the case of a vertical vibration, the depth of focus that is always present means that a slight vibration is not noticed. Horizontal vibrations, however, result in a severe negative impact when observing through the microscope.

SUMMARY OF THE INVENTION

It is the object of the present invention to find solutions which improve the vibratory behavior of the stand, i.e. suppress vibration or optimally damp any vibrations, without thereby sacrificing precise positioning accuracy. The intention in particular is to counteract low-frequency torsional vibrations, e.g. in the range of, for example, 0 to 10 Hz. The new features are intended to effectively counteract torsional vibrations and optionally to be usable in combination with known vibration damping features.

Those skilled in the art know that such objects are difficult to achieve, and that the application of mathematical and physical resources and theories often does not bring the expected results. On the other hand, however, even slight improvements are worth striving for, since they improve convenience for the user and consequently increase operating safety. According to the present invention, this object is achieved by way of a microscope stand, in particular for surgical microscopes, having vertical and horizontal supports and a vibration damper, wherein the vibration damper is configured as a torsional damping element.

The invention thus offers, for the components necessarily present on a stand for a surgical microscope, particularly suitable and tuned damping elements with low weight and improved vibratory behavior. The specifications of stand support parts in terms of their vibratory behavior can be slightly reduced, which in this context can result in cost decreases.

Further specific embodiments and variants thereof are described and protected in the claims. The properties of the preferred material lie within approximately the following parameters:

| | |
|---|---|
| Static modulus of elasticity | 0.2–3 N/mm2; |
| Dynamic modulus of elasticity | 0.5–4 N/mm2; |
| Mechanical dissipation factor | 0.1–0.2; |
| Natural frequency of material | greater than 5 Hz, | measured in each case on the basis of DIN 53513. The preferred material selected is, by way of example, Sylomer® M12, Sylomer® M25 P14 or Sylomer® P12, Sylomer® P25 P15, or in particular Sylodamp® HD-010-11, HD300/1, HD-030-11, HD-050-21, HD-100-11, HD-150-12, HD-300-10 or 12, but preferably HD-300-1 for the dynamic load range from 0 to 0.3 N/mm².

The dissipation factor at 8 Hz per ISO 10846-2 should preferably be more than 0.1, in particular more than 0.2, at a strain at fracture per DIN 53455-6.4 of more than 100%, preferably more than 200%, and in particular approximately 300%.

Such materials are available under the designation SYLODAMP® from Getzner Werkstoffe GmbH, Bürs (Austria).

Damping materials can also be combined if necessary. Variants with specific shaping of the damping materials also lie within the context of the invention. For example, recesses such as blind holes or the like can be provided in order further to influence the damping characteristics.

Sandwich constructions of different damping materials can be used, for example, for improved torsional stiffness.

BRIEF DESCRIPTION OF THE DRAWINGS

The Figures are described continuously. The Description of Figures and the Parts List constitute a unit that is mutually complemented by the other parts of the Specification and the Claims for purposes of a complete disclosure. Identical reference characters denote identical parts. Identical reference characters with different indices denote similar, functionally identical parts. The Figures are exemplary only, and not necessarily depicted in correct proportion.

In the Figures:

FIG. 8 shows a variant of a cylindrical damping element arrangement; and

FIG. 8a shows a section, in plan view, of the arrangement according to FIG. 8.

Figure 1:
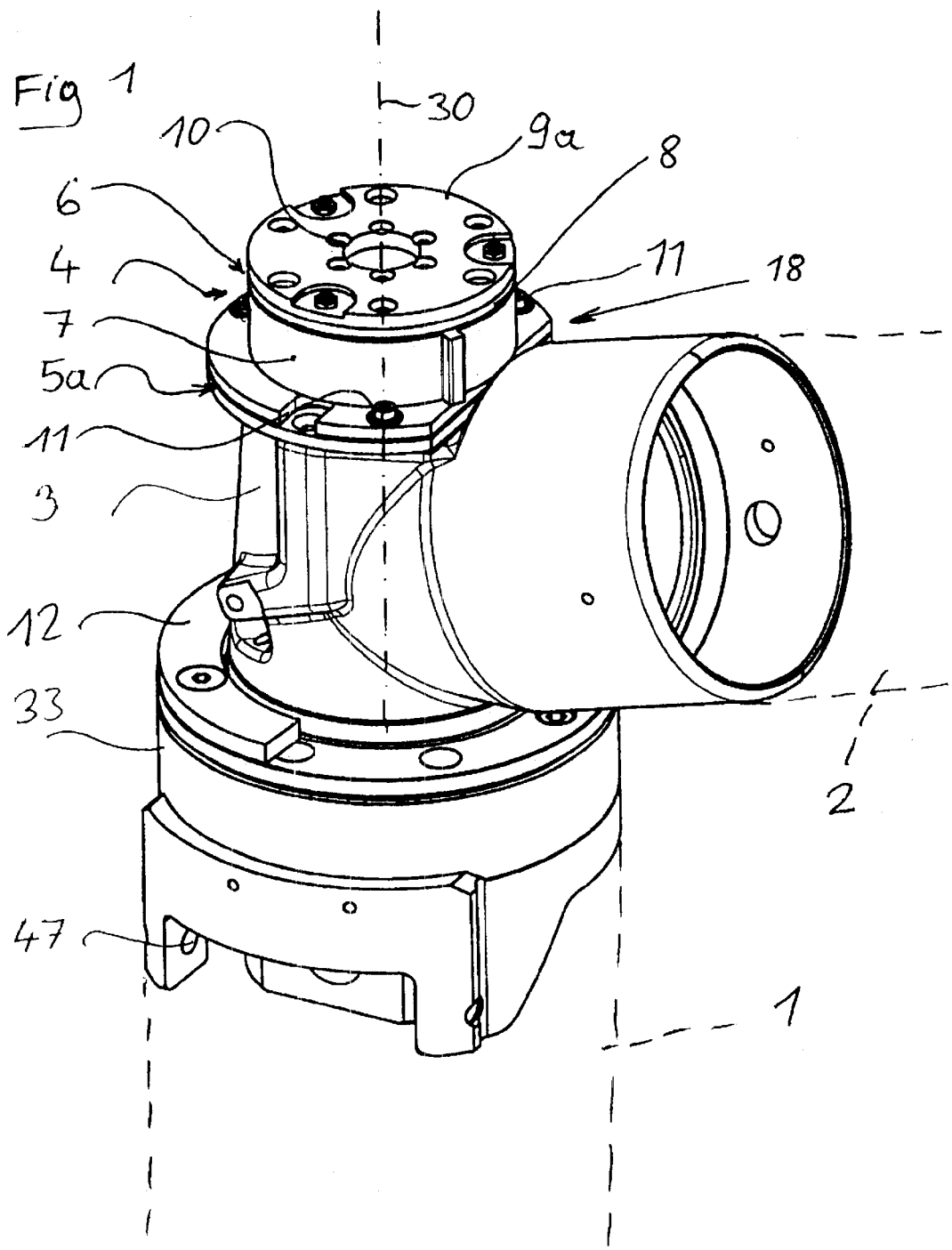
FIG. 1 is an oblique view of a stand rotary bearing according to the present invention, at the transition between the upright column and a carrier arm.

The Figures are described in overlapping fashion. Identical reference characters denote identical objects; identical reference characters with different indices denote components with identical or similar purposes but a different construction. The Parts List is an integral constituent of the Description of Figures.

DETAILED DESCRIPTION OF THE INVENTION

FIG. 1 shows a portion of an implemented configuration of the stand according to the present invention. This configuration is directly linked to U.S. patent application Ser. No. 10/107,548 (claiming priority of German patent application 101 23 166.0 filed Mar. 31, 2001), which application was filed on the same date as the present application, shares the same applicant as the present application, is incorporated herein by reference in its entirety, and which deals with another detail of possible stand equipment.

A bearing sleeve 33—which preferably, according to aforementioned U.S. patent application Ser. No. 10/107,548, can be brought into plumb—that carries a support member 3 is provided on an upright column 1 (merely indicated). Joined to support member 3 is a carrier arm 2 (merely indicated), such as is, for example, labeled 11c in FIG. 12 of aforementioned U.S. patent application Ser. No. 10/107,548. Carrier arm 2 is rotatable about a rotation axis 30 so that it can bring its load (a microscope) into various spatial positions. In order to retain a selected spatial position, a brake 4 is provided which immobilizes carrier arm 2 in the braked state relative to upright column 1. Once the braked position has been reached, even very small lateral alternating forces on the load (microscope) can result in a vibratory excitation that causes the load to oscillate back and forth. In that context, torsional forces take effect in brake 4, in stand column 1, and in the carrier arm itself (as flexural forces). The principal object of the invention is to suppress or compensate for this back-and-forth oscillation as completely as possible. In the configuration shown in FIG. 1, this is brought about by way of a torsional damping element 5a that is arranged between brake engagement surface 6 and support element 3.

Brake 4 substantially comprises a brake body 7 and an armature 8, as well as an armature flange 9a. Brake body 7 is nonpositively connected to support element 3, and armature flange 9a or armature 8 is nonpositively connected to upright column 1. The connection to support element 3 is brought about by way of bolts 11, whereas the connection to upright column 1 is made via bolts 10.

Also secured to upright column 1 is a pivot limiter 12 that, in combination with a stand foot of specific configuration and an equipment box (cf. FIG. 12) of aforementioned U.S. patent application Ser. No. 10/107,548 serving for weight balancing, results in the inventive effect of Patent Application PCT/EP98/03614 (International Publication No. WO 99/01693) and is to that extent also given protection.

Figure 2:
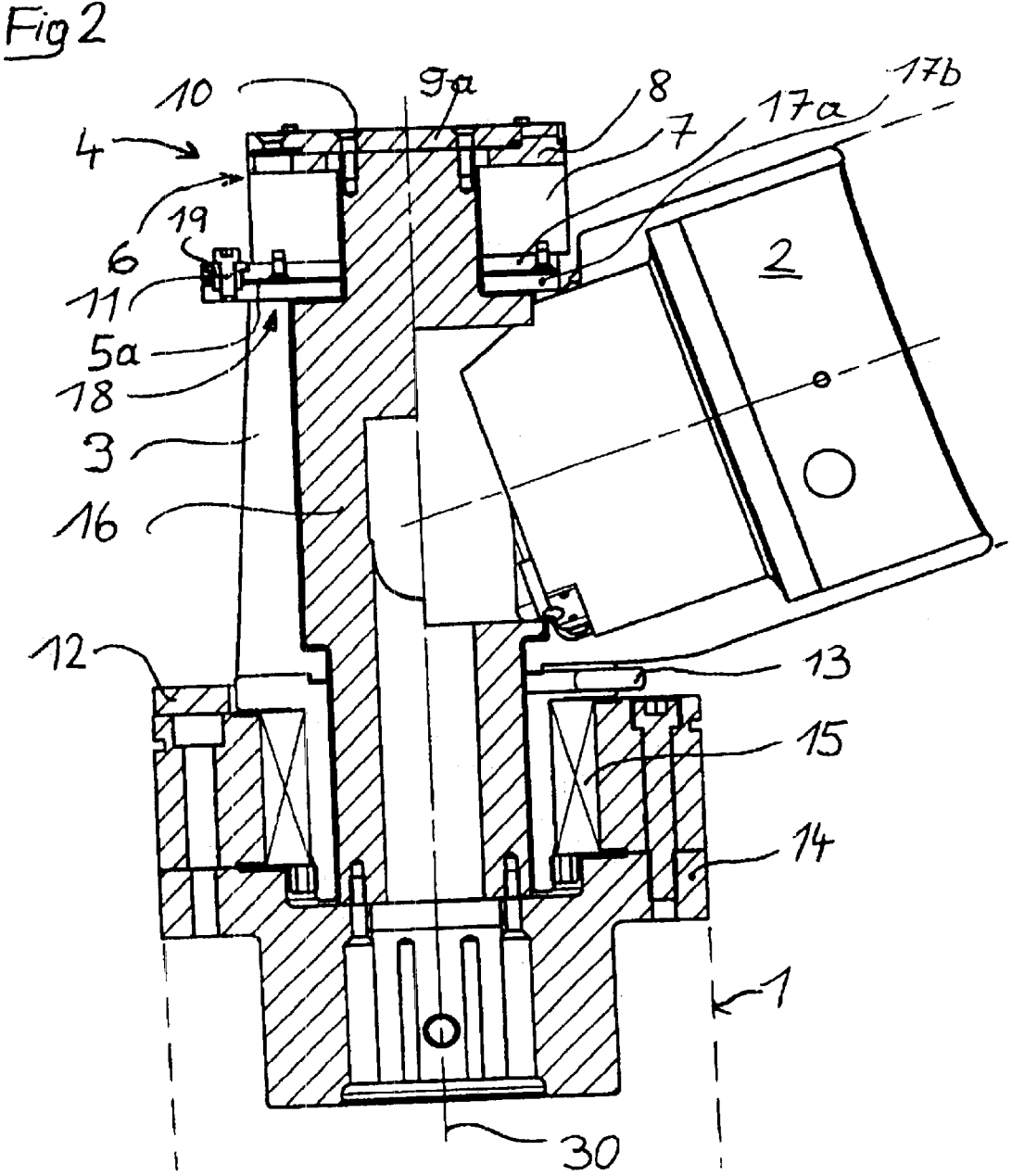
FIG. 2 shows a vertical section through the structure of FIG. 1.
Figure 3:
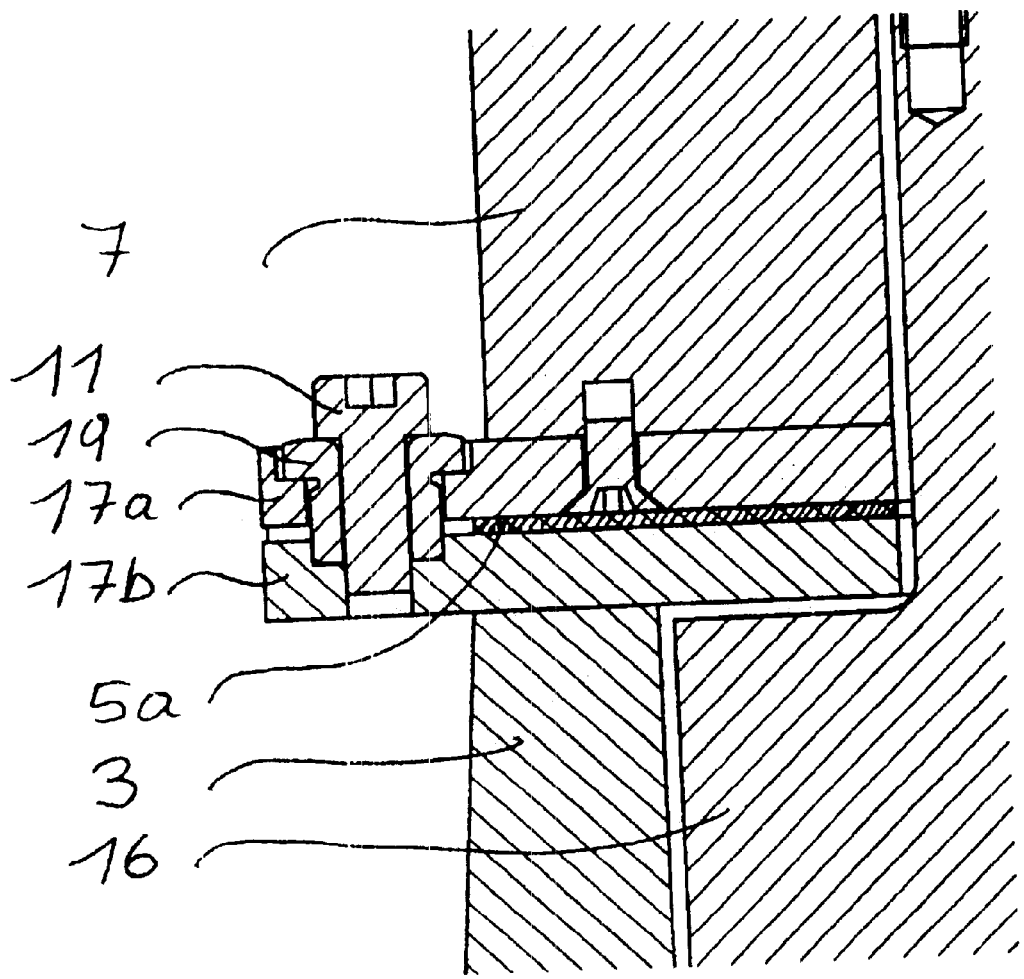
FIG. 3 shows an enlarged detail of FIG. 2.

Pivot limiter 12 coacts with a stop 13 on support element 3 (FIG. 2).

As is better evident from FIG. 2, upright column 1 comprises a bearing block 14 that carries a bearing 15 in which support element 3 is mounted. Located concentrically inside the support element is an armature bracket 16 that is rigidly joined to bearing block 14 and at its upper end supports armature 8 via armature flange 9a. Axis 30 of upright column 1 thus constitutes the rotation axis for support element 3 and thus for carrier arm 2.

The context of the invention of course also encompasses any other assemblages in which no upright column, or a different upright column, is provided, or in which the function of the upright column is assumed by other components, e.g. in ceiling mounts, the ceiling column; or in wall mounts, the wall retainer; or in stands having multiple carrier arms, one of the latter.

The manner of operation of brake 4 (which is electromagnetic in this case) and of the assemblage according to the present invention is as follows: when brake 4 and brake body 7 are in the unenergized state, as depicted in FIG. 2, armature 8 rests against brake engagement surface 6 on brake body 7. No rotation is therefore possible between support element 3 and armature bracket 16 (and therefore upright column 1). The braking force is thus transferred from upright column 1 via bearing block 14 into armature bracket 16, and from there via armature flange 9a to armature 8 and brake body 7, then being transferred from the latter via a damping flange 18 to support element 3 and thus to carrier arm 2.

Damping flange 18 comprises an upper and a lower flange 17a, b, between which damping element 5a is inserted or adhesively bonded. The upper and lower flanges are separated by spacer sleeves 19 that on the one hand make possible a certain preload between the two flanges, but on the other hand also, as a result of a corresponding elongated hole or hole size configuration, also offer a capability of rotation relative to one another about axis 30.

Spacer sleeves 19 also prevent torsional damping element 5a from being loaded in tension when the brake is open. This relieves stress on the adhesive bond if, as is preferred, the torsional damping element is adhesively bonded onto flanges 17.

Armature 8 itself is not depicted in further detail, but is spring-loaded as is usual in such brakes.

The rotation capability about spacer sleeves 19 creates a clearance that allows carrier arm 2 to pivot slightly even when brake 4 is applied. Torsional damping element 5a counteracts this pivotability with its torsional resilience. In the preferred embodiment, this resilience results in approximately 100% return of a carrier arm 2 moved in the tolerance range. The specific configuration and material selection for torsional damping element 5a result in the vibration-damping properties of the assemblage.

Figure 4:
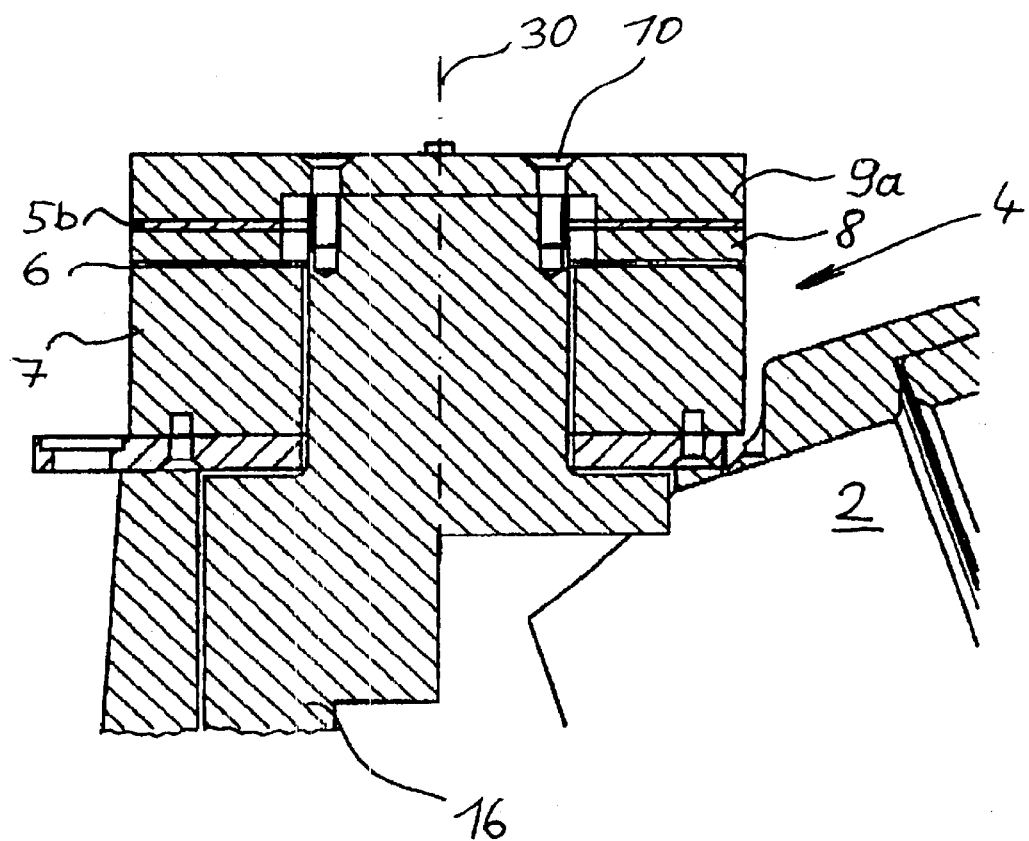
FIG. 4 shows a variant with a modified position of the damping material.

The assemblage as shown in FIG. 4, in which torsional damping element 5b is adhesively bonded between armature 8 and armature flange 9a, is not substantially different. What is disadvantageous about this assemblage, as compared to the one first described, is the fact that torsional damping element 5b is loaded in tension when brake 4 is applied (i.e. most of the time), which could be disadvantageous for the bonded surfaces.

Figure 5:
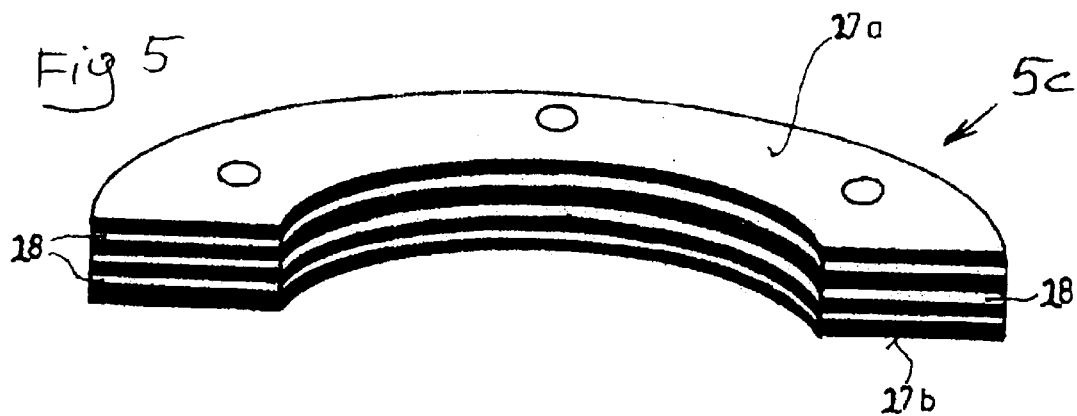
FIG. 5 shows a sandwich that combines several damping layers.

Torsional damping element 5c depicted in FIG. 5 comprises multiple damping layers 28 made of damping material, and metal washers 27a and 27b joined thereto in sandwich fashion. Such sandwich assemblages are usable in the context of the invention as necessary, and the detailed material choice made by the user depends on the particular requirements in terms of the application and damping. Softer or harder damping materials can be used depending on whether the user desires softer or harder resilience characteristics, more or less damping, or more or less play. The damping materials preferred according to the present invention are recited in the specification and in the claims.

According to a particular embodiment of the invention, the torsional damping element made of a series of different elements is replaceable and/or its preload is adjustable, so that a user can himself select the degree of damping.

FIG. 8 shows an assemblage similar to the assemblages described earlier. Armature flange 9b is differently configured, however, in that it directs a pivot pin 29 downward against an armature follower 26 that concentrically surrounds the latter. A rotational clearance, which is damped by a sleeve-shaped torsional damping element 5d, is thus possible between armature follower 26 (which assumes some of the functions of armature bracket 16) and the pivot pin.

FIG. 8a shows a section through the region of torsional damping element 5d in the assemblage of FIG. 8.

Figure 6:
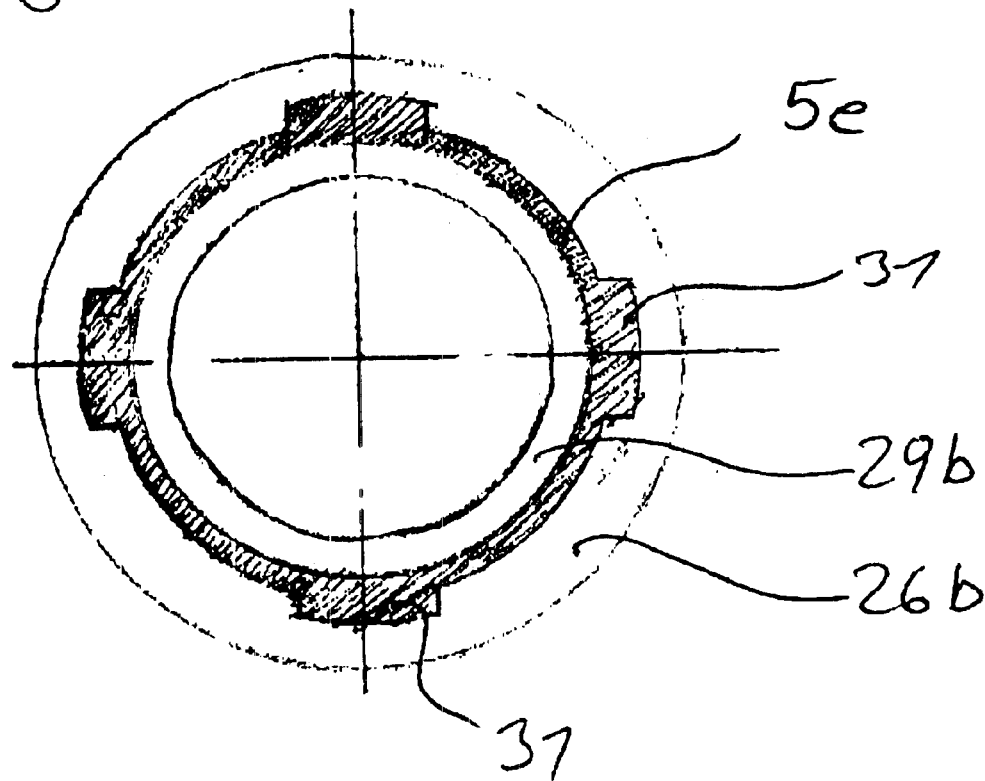
FIG. 6 symbolically depicts another damping element.
Figure 7:
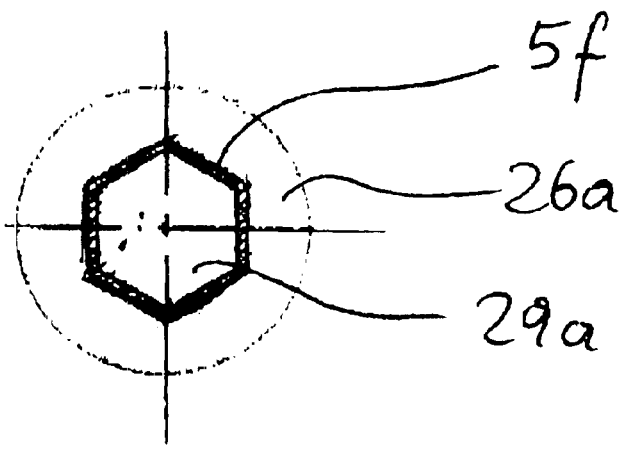
FIG. 7 shows a variant of the element according to FIG. 6.

FIGS. 6 and 7 indicate variants of the assemblage shown in FIG. 8, in which there is a departure from the principle of pure shear loading in the torsional damping element, and instead tension-compression components are also used in the particularly configured torsional damping element 5e, 5f.

Torsional damping element 5f shown in FIG. 7 is an element made up of a polygonal tube that is inserted or adhesively bonded into a congruent cavity between two mutually rotatable parts and is thus loaded on the one hand slightly in shear, and in tension-compression.

In torsional damping element 5e shown in FIG. 6, a tubular element is provided between two mutually rotatable parts and is in that respect loaded in shear, while radially projecting lugs 31 engage into counterpart recesses in the mating part and thus can be loaded in tension-compression and can develop their respective individual damping characteristics.

Parts List
1 Upright column
2 Carrier arm
3 Support member
4 Brake
5a –f Torsional damping element
6 Brake engagement surface
7 Brake body
8 Armature
9a, b Armature flange
10 Bolts
11 Bolts 12 Pivot limiter
13 Stop
14 Bearing block
15 Bearing
16 Armature bracket
17a, b Flange
18 Damping flange
19 Spacer sleeves
26a, b Armature followers
27, 27a, b Metal washers
28 Damping layers
29 Pivot pin
30 Axis
31 Lugs
32 ●
33 Bearing sleeve
34 ●
47 Pivot axis—see aforementioned U.S. patent application Ser. No. 10/107,548 (not essential for the present invention).

What is claimed is:

1. A microscope stand for supporting a surgical microscope, said stand having a vertical support (1), a horizontal support (2) pivotable about a rotational axis (30) relative to said vertical support (1), a brake (4) for holding the horizontal support (2) at a selected pivot position relative to said vertical support, and a vibration damper arranged for reducing transmission of angular vibrations between said vertical and horizontal supports (1, 2), wherein the vibration damper is configured as a torsional damping element (5) acting with respect to annular displacements about said rotational axis (30), said torsional damping element (5) having a resilience so great that it brings about at least 90% return of a stand component displaced against the annular direction of action of the torsional damping element when said brake is applied.

2. The stand as defined claim 1, wherein vibration travel limiters (12, 13) are provided to limit pivot displacement of said horizontal support (2) relative to said vertical support (1) about said rotational axis (30).

3. The stand as defined in claim 1, wherein the torsional damping element (5) is arranged in such a way that it is stressed in shear.

4. The stand as defined in claim 1, wherein the torsional damping element includes at least one damping plate.

5. The stand as defined in claim 4, wherein said torsional damping element includes multiple damping plates (28) arranged in parallel to form a layered torsional damping element.

6. The stand as defined in claim 5, wherein the layered torsional damping element comprises more than three metal plates and at least one said damping plate (28) in between adjacent metal plates thereof.

7. The stand as defined in claim 1, wherein the damping element (5) is constructed of a cellular plastic foam and preferably exhibits at least one of the following parameters:

Static modulus of elasticity in the range of 0.2–3 N/mm2;

Dynamic modulus of elasticity in the range of 0.5 –4 N/mm2;

Mechanical dissipation factor in the range of 0.1 –0.2;

Natural frequency of material greater than 5 Hz, measured in each case on the basis of DIN 53513;

the dissipation factor at 8 Hz per ISO 10846-2 being greater than 0.1; and strain at fracture per DIN 53455-6.4 being greater than 100%.

8. The stand as defined in claim 1, wherein the damping element is arranged between two components of said stand rotatable relative to one another, and said torsional damping element is adhesively bonded to said two components of said stand.

9. The stand as defined in claim 1, wherein the damping element (5d–f) is configured as a damping sleeve that is adhesively bonded in between two mutually rotatable components (26, 29).

10. The stand as defined in claim 1, wherein the damping element (5e, f) is arranged between two mutually rotatable components (29a, b and 26a, b) in such a way that it is loaded in compression.

11. The stand as defined in claim 1, wherein the damping element (5) is constructed of at least two materials (27, 28) having substantially different moduli of elasticity.

12. The stand as defined in claim 1, wherein the damping element (5) is mounted directly or indirectly on a rotary-force-transferring part of said brake (4) and is joined in series to the brake (4).

13. The stand as defined in claim 12, wherein the damping element (5) is unloaded in the braked state.

14. The stand as defined in claim 1, wherein the damping element (5) is kept free of axial forces.

* * * * *